United States Patent
Rytter et al.

(10) Patent No.: US 6,809,121 B1
(45) Date of Patent: Oct. 26, 2004

(54) COGENERATION OF METHANOL AND ELECTRICAL POWER

(75) Inventors: Erling Rytter, Trondheim (NO); Ola Olsvik, Hundhammeren (NO)

(73) Assignee: Statoil Asa, Stavanger (NO)

( * ) Notice: Subject to any disclaimer, the term of this patent is extended or adjusted under 35 U.S.C. 154(b) by 9 days.

(21) Appl. No.: 10/130,539

(22) PCT Filed: Nov. 20, 2000

(86) PCT No.: PCT/NO00/00389

§ 371 (c)(1), (2), (4) Date: Sep. 23, 2002

(87) PCT Pub. No.: WO01/36357

PCT Pub. Date: May 25, 2001

(30) Foreign Application Priority Data

Nov. 19, 1999 (NO) .......................................... 19995679

(51) Int. Cl.[7] .............................. C07C 27/00; C01B 3/12
(52) U.S. Cl. ................. 518/700; 508/702; 508/703; 508/704; 423/655
(58) Field of Search .................. 518/700, 702, 518/703, 704; 423/655

(56) References Cited

U.S. PATENT DOCUMENTS

| 4,946,477 A | | 8/1990 | Perka et al. |
| 5,496,859 A | | 3/1996 | Fong et al. |
| 5,624,964 A | | 4/1997 | Cimini et al. |
| 5,799,482 A | | 9/1998 | Marler et al. |
| 5,980,857 A | * | 11/1999 | Kapoor et al. ........... 423/648.1 |
| 6,110,979 A | * | 8/2000 | Nataraj et al. ............. 518/704 |

FOREIGN PATENT DOCUMENTS

| WO | 98/32817 | 7/1998 |
| WO | 98/36038 | 8/1998 |

* cited by examiner

Primary Examiner—J. Parsa
(74) Attorney, Agent, or Firm—Wenderoth, Lind & Ponack, L.L.P.

(57) ABSTRACT

A process for the production of methanol and/or dimethyl ether and/or other xygenates thereof, a $H_2$-rich and a $CO_2$-rich stream and an integrated plant for the production in said process of methanol and/or dimethyl ether and/or other oxygenates thereof, a $H_2$-rich and a $CO_2$-rich stream. The use of $H_2$ formed by a shift reaction in a shift reactor for the reduction of CO and $CO_2$ in a methanol synthesis reactor is disclosed.

18 Claims, 1 Drawing Sheet

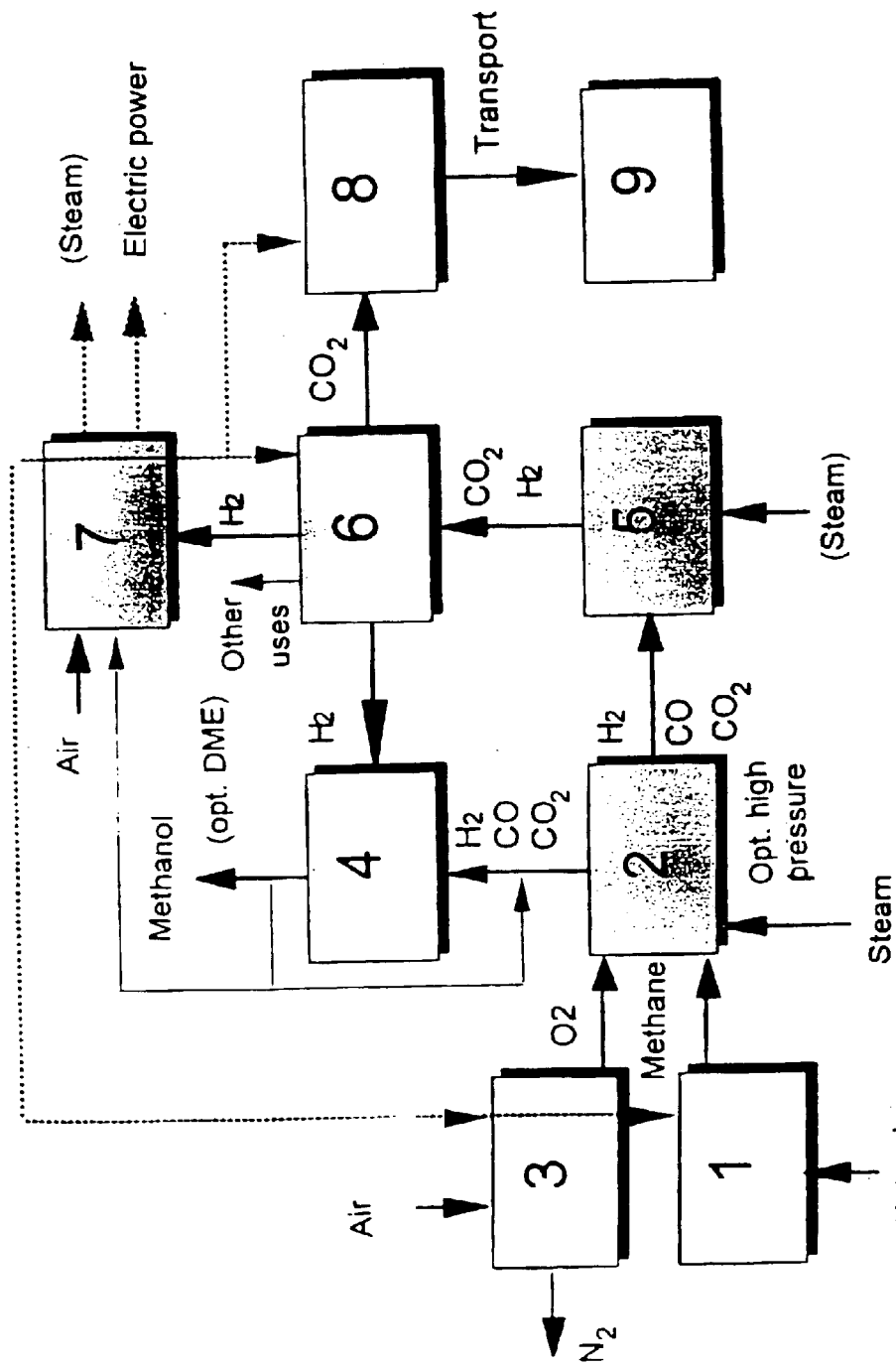

COGENERATION OF METHANOL AND ELECTRICAL POWER

The present invention relates to a process of the production of methanol and/or dimethyl ether and/or other oxygenates thereof, an $H_2$-rich and a $CO_2$-rich stream. Further, the invention relates to an integrated plant for the production by said process of methanol and/or dimethyl ether and/or other oxygenates thereof, a $H_2$-rich and a $CO_2$-rich stream. The invention also relates to the use of $H_2$ formed by the shift reaction in a shift reactor for the reduction of CO and $CO_2$ in a methanol synthesis reactor. A flexible use of hydrogen in such a plant and for different uses is disclosed.

Due to the continually stricter requirements of improved environment and reduced emissions, it is supposed that the products produced by the technology disclosed will achieve increased use and importance. For example methanol in addition to several uses in the chemical industry, may be fed to combustion cell driven vehicles. This will reduce the emission of particles, $NO_x$, $SO_x$ and VOC down close to zero values and thereby be particularly important for the improvement of the environment in urban areas. Compared to the conventional motor technology, also the emission of climate gases will be reduced, e.g. by 50%. Several large automobile manufacturers are investing highly to develop and commercialise this technology. DME will correspondingly be a particularly environmentally friendly fuel for the diesel combustion vehicles of today. Fleet tests show that this is absolutely practicable. Hydrogen is frequently referred to as the energy carrier of tomorrow. It is certain that there will exist a significantly increasing hydrogen demand in the refinery industry to remove sulphur and reduce the contents of aromatics and olefins in the fuels produced. A possible new use is as fuel for gas turbines of heat generating stations to thus considerably reduce the emission of $CO_2$ in the production of electrical power.

It is generally accepted that the greenhouse effect and the climate on the earth has a close connection to the human produced $CO_2$ emissions, and the reduction thereof is therefore desirable. In the production of methanol or dimethyl ether or any other hydrocarbon containing oxygenates a synthesis gas can be used comprising a mixture of hydrogen, carbon monoxide and carbon dioxide. In spit of $CO_2$ thus being included as a part of the synthesis step, a total excess of $CO_2$ will be formed being emitted to the atmosphere, e.g. by the burning of natural gas in a steam reformer. The U.S. Pat. No. 4,946,477 describes an IGCC process having a combined methanol synthesis/water gas shift for methanol and electrical power production. An improvement is described by the preparation of methanol from a synthesis gas comprising carbon monoxide and hydrogen by using a three phase or liquid phase reaction technique. The improvement of the process resides in addition of relatively small amounts of water to the liquid phase reactor thus allowing use of a CO-rich synthesis gas for the production of methanol by performing methanol synthesis and water-gas shift reactions in the same reactor.

The tables of said patent indicates that $CO_2$ from significant amounts of $CO_2$ are emitted with the turbine exhaust gas.

U.S. Pat. No. 5,799,482 relates to a process of enhanced heat integration of an oxidant supplemented autoterm reformer and co-generation power station. However, the patent does not relate to the production of methanol.

The U.S. Pat. No. 5,624,964 relates to the integration of a steam reforming unit and a co-generation power station. Neither does this patent relate to a methanol synthesis.

U.S. Pat. No. 5,496,859 relates to a gasification process combined with steam methane reforming to prepare syngas useful for methanol production. An integration with power stations or other hydrogen operated stations does not appear to be disclosed.

A particularly compact and efficient mode of synthesis gas production is by the autothermic reformation (ATR) of natural gas. In an autothermic reformer natural gas is fed with oxygen, air or enriched air, into a combustion chamber. The energy required to operate the endothermic steam reformation reactions is provided by the exothermic reactions between hydrocarbons and/or hydrogen and oxygen. The temperature of the combustion chamber itself may reach above 2000° C. Following the combustion chamber, the reaction is brought to equilibrium above a catalyst bed before the synthesis gas escapes the reactor at about 1000° C. The size of such a unit will typically be 10 to 15 meter high, having a diameter of 5 to 6 meter. The steam/carbon ratio may be 0.6 to 1.4 or higher. Such an ATR may be operated at e.g. 40 bar or higher. For particular purposes a high pressure may be desirable.

However, the stoichiometry of methanol production provides for the stoichiometric ratio $SN=(H_2-CO_2)/(CO+CO)$ being like 2, whereas ATR will provide for a ratio SN of below 2. This requires that also at ATR $CO_2$ has to be emitted at some site.

Further, there will be different requirements of energy to operate a methanol plant. This relates to the option of separation of air, as well as preheating natural gas and methane, and what shall be shown, to separate and compress $CO_2$. A possibility of providing this energy is by the combustion of hydrocarbons, a.o. by the generation of electrical power in gas turbines, which again results in the formation of $CO_2$.

A feasible way to obtain reduced emissions by the production of methanol (or DME) would be to convert the fuel, e.g. natural gas, into a mixture of hydrogen and carbon oxides by ATR technology, use parts of this gas stream to produce methanol, whereas the other part is shifted to hydrogen and carbon dioxide, separating these two components, using the hydrogen as fuel in a gas turbine and to adjust the stoichiometric relation in methanol production, and to deposit carbon dioxide subsequent to compression to the desired pressure. This deposition may take place on the seabed or in geological reservoirs. These reservoirs may include hydrocarbons. Depending on the requirement of methanol and/or energy, the total energy balance, local conditions, the value of the single product streams etc., the ratio between said synthesis gas streams may be varied liberately. As an extreme it will not be necessary to produce electrical power in a gas turbine.

Such a technology as disclosed above is costly and will result in a smaller energy yield than a conventional, but modern production plant. It is thus a challenge to design the process as economically optimal as possible and reduce the energy consumption to a minimum, a.o. through heat integration and an optimal steam balance. To achieve this it may be suitable to operate the single process steps in a different and simpler way than usual if hydrogen, carbon monoxide or synthesis gas are to be used in industry, e.g. in petrochemical industry or by refining raw oil. This profit in simplified plants may be achieved by allowing that a limited part of the carbon feed stock resides in the form of methane or carbon monoxide when the hydrogen-rich gas mixture is fed as a fuel to the gas power station. The reforming of natural gas, shift of carbon monoxide to carbon dioxide as well as the separation of carbon dioxide will thus be feasible at conditions beneath those being generally accepted in industry and recommended in textbooks.

A particularly beneficial result of the reduced requirement of methane and carbon monoxide in the product gas will be the possibility of operating one or more process steps at a higher pressure. Thereby a reduction in costs and in the compression energy of $CO_2$ prior to deposition is obtained. It may thus also be possible to separate and compress $CO_2$ in a liquid form, which may result in further savings. Other savings result in the possible use of lower temperatures in reforming than would else be required at a given pressure. Further if both low temperature shift and methanisation of residual carbon monoxide may be unnecessary, different from what is standard technology today in the production of hydrogen for the synthesis of ammonia. If separating $CO_2$ in an amine washing process is selected, this may be simplified, e.g. by only using a limited depressuration instead of steam stripping.

The following chemical reactions are central in the production of synthesis gas, methanol and hydrogen in the reformation of natural gas:

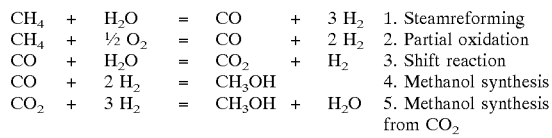

| | | | | | | |
|---|---|---|---|---|---|---|
| $CH_4$ | + | $H_2O$ | = | $CO$ | + | $3 H_2$ | 1. Steamreforming |
| $CH_4$ | + | $½ O_2$ | = | $CO$ | + | $2 H_2$ | 2. Partial oxidation |
| $CO$ | + | $H_2O$ | = | $CO_2$ | + | $H_2$ | 3. Shift reaction |
| $CO$ | + | $2 H_2$ | = | $CH_3OH$ | | | 4. Methanol synthesis |
| $CO_2$ | + | $3 H_2$ | = | $CH_3OH$ | + | $H_2O$ | 5. Methanol synthesis from $CO_2$ |

The reaction heat of the strongly endotherm steam reformation may be provided either by external burning or by the combination of the exothermic partial oxidation in an autotherm reformer. A purely partial oxidation of the combined reforming may also be used.

BRIEF DESCRIPTION OF THE DRAWING

The FIGURE shows an example of how a process having the abovementioned benefits may be designed. Due to equilibrium restrictions it is conventional, but not required, to recirculate non-reacted synthesis gas. Hydrogen may also be withdrawn for other purposes such as upgrading product streams in a refinery and for the use as an energy carrier in transport means. It will also be required having a purge to avoid accumulation of inerts in the methanol synthesis. This stream may be passed to the power station, the shift reactor or to the $CO_2$ separator depending on what is suitable. Normally the separation of air into the main component nitrogen and oxygen by the production of methanol is selected. This nitrogen may be used in different ways, as a supplement to hydrogen before the feeding into the gas turbine to avoid overheating and backfire, and to increase the gas stream into an oil reservoir if beneficial.

DETAILED DESCRIPTION OF THE INVENTION

The objects of the instant invention are achieved by a process of the kind defined in the introduction for the production of methanol and/or dimethyl ether and/or other oxygenates thereof, and a $H_2$-rich and a $CO_2$-rich stream, which comprise the combination of the following steps:

The preparation of a synthesis gas comprising substantially $H_2$, $CO$, $CO_2$ and small amounts of methane in a reformation plant by feeding lower hydrocarbons and steam to the reforming plant:

splitting of the synthesis gas into two streams, one of which is used as feed to one or more reactors for the synthesis of methanol and/or dimethyl ether and/or other oxygenates thereof, whereas the other stream is passed to one or more shift reactors, in which it is subjected to a shift reaction by converting CO with steam, passing the shift d gas stream substantially comprising $H_2$ and $CO_2$ to a separation plant and subjecting it to a separation therein into two streams substantially comprising $H_2$ and $CO_2$ respectively, at least 5% of substantially $H_2$-containing stream being fed—optionally as partial streams—to the methanol synthesis reactor(s), and the remaining part of the $H_2$-containing stream to one or more heat-generating station(s) or to other $H_2$-requiring processes.

Preferable the reforming plant includes at least one autothermic reformer.

Particularly preferred the reforming plant consists of an autothermic reformer combined with a steam reformer and a prereformer.

It is preferred that the methanol reactor is supplied with such an amount of hydrogen that the optimal achievable stoichiometric number $SN=(H_2—CO_2)/(CO+CO_2)$ is achieved, and particularly that such an amount of hydrogen is supplied to the methanol reactor that a SN>1,9 is achieved.

Further, the autothermic reformer may suitable be supplied with an oxygen containing gas stream, and particularly using substantially pure $O_2$ as an oxygen containing gas.

Particularly the autothermic reformer will be fed natural gas as natural gas as a lower hydrocarbon gas, and it may beneficially be a prereformed natural gas.

For environmental and practical purposes, it is preferred that the mainly $CO_2$ containing stream from the separation means are passed to a subterranean or submarine reservoir or optionally deposited in another way.

It is suitable that the entire or part of the $H_2$-containing stream not being passed to the methanol synthesis reactor(s), is fed to one or more heat-generating stations.

It may further be preferred that the entire or part of the $H_2$-containing stream which is passed to the methanol synthesis-reactor(s), is fed to upgrading of one or more refinery streams, and as a further alternative that the entire or part of the $H_2$-containing stream not being fed to the methanol synthesis-reactor(s), is fed to the sites of use as energy carriers, e.g. as fuel for transport purposes, or that the entire or part of the $H_2$-containing stream not being fed to the methanol synthesis-reactor(s) is fed to ammonia synthesis.

According to preferred operation conditions, the autothermic reformer is operated at a pressure of at least about 30 bar, and is particularly preferred that the autothermic reformer is operated at a pressure of at least about 60 bar.

According to a possible embodiment of the invention part of the $H_2$-containing stream from the separator for the $H_2$ and $CO_2$ reformer is supplied as fuel.

It may be preferred to use only one high temperature operated shift reactor.

It is beneficial that the separation of $H_2$ and $CO_2$ is performed at a pressure of at least about 3 bar.

Further, it will be beneficial that the streams from the reformer are distributed between the methanol synthesis reactor and heat generating station depending on the demand of methanol, dimethyl ether and oxidation products thereof and electrical power respectively.

The aims of the invention are further achieved by an integrated plant for the production of methanol and/or dimethyl ether and/or other oxygenates thereof and a $H_2$ stream and a $CO_2$ stream, comprising:

a reformation plant having a supply of hydrocarbons, of steam and air, oxygen enriched air or oxygen, an outlet of reaction products to one or more methanol synthesis reactors and an outlet to a shift reactor, the shift reactor having a supply from said reformer and supply optionally of steam, as well as outlet of reaction products to a separator, a separator having supply from said shift reactor and having an outlet of $H_2$ gas to said methanol synthesis reactor(s) and to a hydrogen power station or other hydrogen requiring plants or transport means.

Optionally the plant comprises means for passing $CO_2$ to one or more compressors, one or more compressors for the compression of $CO_2$, and further transport lines from these to deposition sites of $CO_2$.

The integrated plant further comprises a pre-treatment plant for hydrocarbon material being fed to the reformation plant.

This pre-treatment plant is particularly a pretreatment plant of natural gas.

Further, the integrated plant comprises preferably an air separation plant for the feed of $O_2$ enriched gas to the reformer.

In the integrated plant the reforming plant comprises preferably at least one autothermic reformer, but it is also possible to use a different reformer technology.

The FIGURE shows an integrated plant for the production of methanol and similar, and a $H_2$-rich and a $CO_2$-rich stream, wherein the different components and streams of the plant are shown.

In the plant as indicated on the enclosed FIGURE, natural gas and steam are fed into a pre-treatment plant 1. This is also supplied with energy, for example by heating the feed. From the pre-treatment plant 1 substantially a methane stream (comprising some $CO_2$), is withdrawn, which is passed to a reformer 2. This is preferably an autothermic reformer. The reformer 2 is optionally further supplied with steam and is optionally kept under high pressure. Further, the reformer is supplied with oxygen or oxygen-enriched air from any air separation plant 3, from which nitrogen ($N_2$) is withdrawn as a secondary stream. From the reformer 2 two streams are withdrawn. The first stream consisting of hydrogen ($H_2$), carbon monoxide (CO) and carbon dioxide ($CO_2$) is fed to a shift reactor, which may also be fed further steam. In the shift reactor a shift reaction is carried out under shift reaction conditions, and as a product stream from the shift reactor a stream mainly consisting of carbon dioxide and hydrogen gas is withdrawn, which is passed to a separation plant 6. In the separation plant 6 the mixture is separated in a carbon dioxide stream and one or more hydrogen gas streams. The other gas stream from the reformer 2 likewise consisting of hydrogen gas ($H_2$), carbon monoxide (CO) and carbon dioxide ($CO_2$) is passed to a methanol synthesis plant 4. This methanol synthesis plant is also supplied with a hydrogen gas stream from the separator 6 to complete the hydrogen requirement in the synthesis of methanol, optionally dimethyl ether or other oxygenates of methanol. From the methanol synthesis plant a product stream mainly consisting of methanol or optionally dimethyl ether or other oxygenates, are withdrawn, depending on the operation conditions, the catalyst used and the stoichiometric ratio between the supplied streams. Depending on the actual preferred embodiment, the streams from the reformer 2 and the subsequent plant might also contain steam and nitrogen and other inert components as well as residual non-reacted methane.

The product stream including mainly carbon dioxide from the separator 6 may be compressed in a compression plant 8 and transported from this to deposition. The surplus of the hydrogen, which is separated in the separator 6, may be passed to a hydrogen power station 7, which is also supplied with air for the combustion of the hydrogen gas to steam producing electrical power. An optional depressurating gas from the methanol plant including hydrogen, carbon monoxide and carbon dioxide may be recycled to the power station as a supplement.

Energy from the hydrogen power station 7 may be used in the air separator 3, in the separator 6 for separation of hydrogen and carbon dioxide, and for the compression of carbon dioxide from the separator 6.

The exercise of the invention.

In a steam reformer (SR) natural gas (methane) is converted in a tube reactor at high temperature and restricted pressure. A steam reformer consists of a great number of reactor tubes, 200–250 tubes having a relative length of 12–13 meter, an internal diameter of about 10 cm and external diameter of about 12 cm. This is a space requiring unit having a length of 30–40 meter, width of 10–12 meter and hight of 15–20 meter. Conventional steam reformers are operated in the pressure area from 15 to 30 bar. The outlet temperature of the gas from a conventional steam reformer is in the temperature range 950° C. The energy that is used to operate the endothermic reactions is supplied by external burning/heating (top, side, bottom or terrace-burned). The ratio between steam and carbon is from 2.5 to 3.5, and the ratio between hydrogen and carbon monoxide in the product stream is from 2.7 to 3.0. A typical synthesis gas produced from a steam reformer includes about 3 percent/volume methane.

In the present invention the reformation of natural gas (equation 1 and 2 above) takes place in an autotherm reformer (ATR). In an ATR natural gas (methane) is fed together with oxygen/air into a combustion compartment. The energy required to operate the endothermic steam reforming reactions is provided by the exothermic reactions between hydrocarbon/hydrogen and oxygen/air. The temperature of the combustion compartment may amount to above 2000° C. Subsequent to the combustion compartment, reactions are run to equilibrium above a catalyst bed before the synthesis gas leaves the reactor at about 1000° C. The size of such a unit may be 10 to 15 meter high and having a diameter of 5 to 6 meter. A typical ratio of steam:carbon is from 0.6 to 1.4. The ratio between hydrogen and carbon monoxide is lower than 2. A typical methane emission is 1 to 2 percent by volume in the product steam. The ATR may be operated at a higher pressure than the SR.

The present invention can also take place in a partial oxidation reactor (POX) which is also an autotherm reformer, additionally the unit does not include a catalyst bed. This unit is frequently somewhat larger if the same capacity compared to an ATR is to be maintained. The rationale of a somewhat larger reformer is that the ATR has a catalyst accelerating the endothermic reactions. The outlet temperature of a POX is also somewhat higher than of a typical ATR.

The reforming of natural gas may also occur by combined reforming (CR) which is a combination of a steam reforming (SR) and an autotherm reforming (ATR). A combination of SR and ATR enables an adjusted composition leaving the reforming unit by regulating the feeding of the two reformers. SR is in CR run at "milder" conditions, i.e. lower outlet temperature leading to a high methane emission. The rest of the methane is reacted in the ATR. The ratio of steam-carbon is in the range of 1.8–2.4 with a ratio between hydrogen and carbon monoxide in the product gass of above 2.

New reactor types which may be of interest have the designation compact reformers or convective reformers.

After reforming the natural gas, the gas mixture is shifted according to the present invention. The gas mixture from the reforming reactor includes mainly the following gas components: CO, $H_2$, $H_2O$, CO2 and somewhat $CH_4$. There is an equilibrium relation between the four main components given by the stoichiometric equation:

$$CO+H_2O=CO_2+H_2.$$

This reaction is denoted the water/gas shift-reaction, and by operating a shift reactor at specified conditions, the equilibrium may be forced to the right and a gas mixture is achieved being rich on hydrogen and carbon dioxide, and wherein the concentration of carbon monoxide is low. A sufficient velocity of the reaction is provided by using suitable catalysts, and in processes where a high conversion of CO (i.e. ammonia synthesis) is desired, two fixed bed reactors in series are used, high temperature shift reactor and low temperature shift reactor respectively. Two steps are selected because the equilibrium is favoured by high temperature. By selecting two reactors in series, run at different temperatures a reduced total reactor volume is achieved. The process is approximately pressure independent and normally the same pressure as in the reformer is used. Typically the temperature at the outlet of the first reactor is 420° C. and the outlet from the second reactor 230° C. The catalyst in the first step is usually chrom/iron based, while the catalyst in the second step is usually a copper/zink catalyst.

In the shift unit CO and $H_2O$ are reacted to $CO_2$ and $H_2$, and in the prior art it is often a requirement that said reaction is forced as far to the right as possible, resulting in the least possible CO in the gas mixture leaving the shift unit. A low $CO_2$ content in said gas mixture further results in a high purity of the $H_2$-rich gas stream leaving the separation unit. In the prior art the ratio between $H_2O$:CO is usually about 10:1, which requires the addition of a high amount of $H_2O$ to then achieve a high purity of the $H_2$-rich gas. However, in the present invention higher impurities are acceptable in the $H_2$-rich gas, resulting in a reduced addition of $H_2O$ and further in a simpler shift process. These are factors, which totally result in cost savings in the production of a $CO_2$-rich and $H_2$-rich gas stream. In the present invention it is acceptable having a ratio of $H_2O$:CO of 1:9, preferably from 1.5:4.

If the conversion requirement of CO is moderate, which will be the case if the gas mixture is to be burnt for energy purposes, the shift reaction may be effected in one step. A simple high-pressure shift reactor may then be chosen.

A mixture of gases may be separated more or less completely based on the different properties of the gas molecules. The most usual principles are absorption, adsorption, semi-permeable membranes and cryogenic distillation.

$CO_2$ is an acid gas, and the most used processes to separate said gas from other non-acid gas molecules are absorption. By absorption the different chemical properties of the gas molecules are utilized. By bringing the gas mixture into contact with basic liquid, the acid gases will to a great extent be dissolved in the liquid. The liquid is separated from the gas, and the absorbed gas may then be liberated either by changing the composition of the liquid or changing pressure and temperature. For the separation of $CO_2$ aqueous solutions of alcohol amines are mainly used. The absorption takes place at a relatively low temperature and high pressure, whereas stripping of the gas from the liquid takes place at relatively high temperature and low pressure. When liberating $CO_2$ from the amine phase of the stripping unit, stripping steam is usually used. If the partial pressure of $CO_2$ in the gas in the absorption unit is high, e.g. higher than 15 bar, it is possible to obtain high concentrations in the amine phase, and a high part of the absorbed $CO_2$ may be liberated in the stripping column at an increased pressure, e.g. 5 to 8 bar.

By using one or more semipermeable membrane units, it may be achieved that molecules having different molecular weights and different chemical properties penetrate the membrane at a different rate. This principle may be used for the separation of gases. For the gas mixture in re membranes may be selected rapidly penetrated by $H_2$, whereas $CO_2$ penetrates slowly, whereupon a partial separation of the different gas components is achieved. By combining solid substance membranes and liquid membranes, it is also possible to achieve that $CO_2$ penetrates quickly, whereas $H_2$ is retained. By different separation methods it may be difficult to achieve a complete separation of the different gas components. This is particularly the case when using membranes. For gas mixtures to be burnt a partial separation of hydrogen and $CO_2$ may be sufficient.

Description of the methanol synthesis.

After the water of the methanol synthesis has been condensed, the gas is compressed up to the methanol synthesis pressure being in the range of 35 to 100 bar, —for a larger plant in the pressure range of 75 to 110 bar.

The methanol synthesis loop itself consists of a recycling compressor, a heat exchanger ("inter exchanger") preheating the feed to the synthesis reactors and cooling the product gas, the synthesis reactor(s), a raw methanol separator and a system to recover energy from the exothermic methanol synthesis reactions:

$$CO+2H_2 \rightarrow CH_3OH$$

$$CO_2+3H_2 \rightarrow CH_3OH+H_2O$$

To avoid an accumulation of inert (non-reacting) gases, a part of the gas is removed in a so-called "purge-stream". The synthesis is operated at a temperature in the range of 200 to 280° C., usually in the temperature range of 230 to 260° C. The most frequently used catalyst of this synthesis is a copper-based catalyst.

Several different types of methanol synthesis reactors may be used, such as:
  isothermic tube reactors having a catalyst on the inside of vertical tubes and boiling water at the outside. The heat will then be removed by a partial evaporation.
  adiabatically fixed bed reactors having cooling in between (adiabatic cooler reactor) each reactor step.
  adiabatic reactors having cooling by means of a supplement of a new feed at several levels downstreams in the reactor (quench converter system).
  Fluidised bed reactor.

It is also possible to use the techniques disclosed above by using other embodiments of the process. For instance it may be economical that the entire or parts of the synthesis gas stream is passed through one (or more) through-put reactor (s) for methanol synthesis without recycling. This reactor is termed MUGC (make-up gas converter). Such solutions may contribute to increase the contents of hydrogen (higher SN) into optional following methanol synthesis reactors and thereby utilize the hydrogen in a more optimal way.

In a gas power station natural gas is normally combusted wherein the main component is methane and air in a combustion compartment at an increased pressure. The combustion gases power the turbines providing for the required axis moment of the compressor part (compressing air to combustion compartment pressure) and to the operation of a generator or other mechanical device. Mixing in natural gas takes place in burners, and the design thereof is important to obtain the proper flame temperature and to prevent the formation of undesired combustion products. If a hydrogen-rich gas is used instead of natural gas, several factors will be changed which are important for the design of the burner, the combustion compartment and turbine. The most important ones are combustion energy, the flame displacement velocity, explosion area and spontaneous ignition temperature. These are factors responsible for the fact that a hydrogen rich gas cannot simply be used in a gas turbine being constructed for the combustion of methane. The experiences of the combustion of hydrogen-rich gases are limited, and the technology is available to a restricted extent.

In the present invention it is desirable to deposit separated $CO_2$-rich gas. Large amounts of $CO_2$-rich gas may be deposited by several methods wherein the three most appropriate are the deposition at deep sea, the deposition in deep water reservoirs and the deposition in oil reservoirs wherein the gas simultaneously works as a pressurising agent to increase oil recovery. The two last forms of storage are commercially operated. In these storage forms the $CO_2$ gas must be brought to a high pressure for the transport in pipelines to the deposition well and further to the injection. The injection pressure will be variable, but may be in the range of 50 to 300 bar. If the $CO_2$-rich gas is to be separated at an increased pressure, a considerable compression work may b saved, which is the case in the present invention.

EXAMPLES

An ATR synthesis gas reactor is used. The ratio of oxygen/carbon is set at 0.6 and the inlet gas has a composition $CO_{+2}=2.5$, $CH_4=82$, $C2=9$, $C3=5$ and $C3+=1.5$ mol %. The ratio between steam and carbon in the feed (the S/C ratio) may be variable, and different preheating of the feed gas is used.

TABLE 1a

Composition in mol of dry gas after ATR at a pressure of 80 bar per 100 mol.

|  | S/C = 0.5 | | | S/C = 1.8 | | |
|---|---|---|---|---|---|---|
| T(ut, °C.) | 800 | 1000 | 1200 | 800 | 1000 | 1200 |
| $H_2$ | 40.9 | 59 | 65 | 52.9 | 65.6 | 6.8 |
| CO | 13.4 | 25.9 | 36.3 | 10.7 | 20.8 | 27.1 |
| $CO_2$ | 17.4 | 7.3 | 3.8 | 19 | 10.9 | 6.1 |
| $C_1$ | 28.2 | 7.8 | 1.0 | 17.5 | 2.7 | 0 |

TABLE 1b

Composition in mol of dry gas after ATR at a pressure of 40 bar per 100 mol.

|  | S/C = 0.5 | | | S/C = 1.8 | | |
|---|---|---|---|---|---|---|
| T(ut, °C.) | 800 | 1000 | 1200 | 800 | 1000 | 1200 |
| $O_2/C$ | 0.21 | 0.47 | 0.56 | 0.31 | 0.53 | 0.62 |
| $H_2$ | 48 | 63 | 63.5 | 60.3 | 66.3 | 64.2 |
| CO | 14.7 | 27.4 | 30.6 | 12.3 | 21.2 | 224.5 |
| $CO_2$ | 10.1 | 6.4 | 5.6 | 14.7 | 11.8 | 11.1 |
| $C_1$ | 27.1 | 2.9 | 0.1 | 12.6 | 0.6 | 0.0 |

TABLE 2

Ratio in mol from 1- or 2-step shift reactor per 100 mol dry feed gas from ATR at 80 bar, 1000° C. and S/C = 1.8

|  | Feed gas from ATR | 1 step shift reactor | 2-step shift reactor |
|---|---|---|---|
| T(ut, °C.) | 1000 | 400 | 400 + 250 |
| $H_2$ | 65.6 | 83.6 | 85.0 |
| CO | 20.8 | 2.8 | 0.4 |
| $CO_2$ | 10.9 | 28.9 | 31.3 |
| $C_1$ | 2.7 | 2.7 | 2.7 |
| $H_2O$ | 62.4 | 44.4 | 42 |

TABLE 3

Composition in mol from $CO_2$ separation (amine wash) without use of "stripping steam" per 100 mol of dry ATR synthesis gas.

|  | Feed gas from 1-step shift reactor + $H_2O$ condensation | From absorption column | From stipping column |
|---|---|---|---|
| T(° C.) | 40 | 50 | 120 |
| P(bar) | 80 | 80 | 8 |
| $H_2$ | 83.6 | 83.6 | 0 |
| CO | 2.8 | 2.8 | 0 |
| $CO_2$ | 28.9 | 2.8 | 26 |
| Cl | 2.7 | 2.7 | 0 |
| $H_2O$ | — | — | 11 |

TABLE 4

Distribution of the synthesis gas in percent by volume

|  | To shift reactor | To methanol reactor |
|---|---|---|
| Case 1 | 10 | 90 |
| Case 2 | 50 | 50 |
| Case 3 | 90 | 10 |

TABLE 5

Distribution of streams in moles of dry gas at different synthesis gas splitting per 100 mol dry ATR synthesis gas (80 bar)

|  | Case 1 | Case 2 | Case 3 |
|---|---|---|---|
| To shift reactor | | | |
| $H_2$ | 6.6 | 32.8 | 59.0 |
| CO | 2.1 | 10.4 | 18.7 |
| $CO_2$ | 1.1 | 5.5 | 9.8 |
| $C_1$ | 0.3 | 1.4 | 2.4 |
| From | | | |

TABLE 5-continued

Distribution of streams in moles of dry gas
at different synthesis gas splitting per
100 mol dry ATR synthesis gas (80 bar)

|  | Case 1 | Case 2 | Case 3 |
|---|---|---|---|
| absorption column |  |  |  |
| $H_2$ | 8.4 | 41.8 | 75.2 |
| CO | 0.3 | 1.4 | 2.5 |
| $CO_2$ | 0.3 | 1.4 | 2.5 |
| $C_1$ | 0.3 | 1.3 | 2.4 |
| From stripping column |  |  |  |
| $CO_2$ | 2.6 | 13 | 23.4 |
| To methanol synthesis reactor |  |  |  |
| $H_2$ (from ATR) | 59.0 | 32.8 | 6.6 |
| $H_2$ (from abs. col.) | 7.8 | 4.5 | 0.9 |
| CO | 18.7 | 10.4 | 2.1 |
| $CO_2$ | 9.8 | 5.5 | 1.1 |
| $C_1$ | 2.4 | 1.4 | 0.3 |
| SN | 1.99 | 2.00 | 2.00 |
| Methanol production |  |  |  |
| $CH_3OH$ | 28.5 | 15.9 | 3.2 |
| Net hydrogen production (except to methanol) |  |  |  |
| $H_2$ | 0.6 | 37.3 | 74.3 |
| Equivalent power production (appr.) |  |  |  |
| kWh | 0.02 | 1.5 | 3.0 |

In Table 1a which is the starting point of the subsequent examples, it is a provision that the $O_2/C$ ratio is constantly equal to 0.6. The ATR outlet temperature stated is then obtained by regulating the pre-heating temperature of the feed.

However, in Table 1b a constant pre-heating temperature of 600° C. is used and the $O_2/C$ ratio is adjusted to obtain the desired ATR outlet temperature.

It is a provision that all synthesis gas to the methanol reactor is converted by recycling. To avoid accumulation of inerts, methane inclusive, it will in practise be required to pass smaller streams, e.g. back to ATR, to the power station or to the atmosphere. The amount of methane in the feed gas to the methanol reactor may be substantially reduced by increasing the temperature of the ATR, ref. Table 1. It may also be suitable to feed a slight excess of hydrogen to the methanol synthesis. When calculating the production of electrical power from the surplus of hydrogen at 80 bar pressure, a 60 percent power efficiency is presumed. For a pure hydrogen power station inclusive the deposition of $CO_2$ an power efficiency related to the combustion heat of methane of between 40 and 50 percent may be estimated. Further, it is obvious that extra energy in the methanol production link will be required for preheating, distillation etc. Thus, if only 10 percent of the ATR synthesis gas is passed to the shift reactor (case 1), it is a requirement to import energy to the plant.

What is claimed is:

1. A process for the production of methanol and/or dimethyl ether and/or other oxygenates thereof, an $H_2$-rich stream and a $CO_2$-rich stream and electrical power, comprising the combination of the following steps:

the preparation of synthesis gas substantially consisting of $H_2$, CO, $CO_2$ and small amounts of methane in a reformation plant by feeding lower hydrocarbons and steam to the reformation plant, splitting of the synthesis gas into two streams, whereof the one is used as a feed to one or several reactions for the synthesis of methanol and/or dimethyl ether and/or other oxygenates thereof, whereas the other stream is passed to one or more shift reactors wherein it is subjected to a shift reaction, the shifted gas stream mainly consisting of $H_2$ and $CO_2$, is passed to a separation means and subjected to a separation therein into two streams which substantially contain $H_2$ and $CO_2$ respectively, at least 5% of the substantially $H_2$-containing stream is passed—optionally as part streams—to the methanol synthesis reactor(s), and the remaining part of the $H_2$ containing stream to one or more heat generating station(s) or to other $H_2$-requiring processes.

2. The process of claim 1, wherein the reforming plant includes at least one autothermic reformer.

3. The process of claim 1, wherein the methanol reactor is fed such an amount of hydrogen that the optimal obtainable stoichiometric number $SN=(H_2—CO_2)/(CO+CO_2)$ is obtained.

4. The process of claim 1 for the preparation of methanol, wherein such an amount of hydrogen is fed to the methanol reactor that $SN>1.9$ is achieved.

5. The process of claim 1, wherein the substantial $CO_2$ containing stream from the separation means is passed to a subterranean or submarine reservoir or optionally deposited in another way.

6. The process of claim 2, wherein the autothermic reformer(s) further is fed an oxygen-containing gas stream.

7. The process of claim 1, wherein the reforming plant is fed a lower hydrocarbon gas natural gas.

8. The process of claim 1, wherein the entire or a part of the $H_2$-containing stream which is not passed to the methanol synthesis reactor(s) is passed to one or more heat generating stations.

9. The process of claim 2, wherein the autothermic reformer(s) is operated at a pressure of at least 30 bar.

10. The process of claim 9, wherein the autothermic reformer(s) is operated at a pressure of at least 60 bar.

11. The process of claim 1, wherein a part of the $H_2$-containing stream from the separator for $H_2$ and $CO_2$ is fed to the reforming plant as a fuel.

12. The process of claim 1, wherein only one high temperature operated shift reactor is used.

13. The process of claim 1, wherein the separation of $H_2$ and $CO_2$ is effected at a pressure of at least 3 bar.

14. The process of claim 1, wherein the stream from the reformer is distributed between the methanol synthesis reactor and the heat generating station dependent on the requirement of methanol, dimethyl ether and oxidation products thereof and electrical power respectively.

15. The process of claim 1, wherein nitrogen or a stream enriched in nitrogen from an air separation plant is fed to the heat generating station.

16. The process of claim 1, wherein nitrogen from an air separation plant is passed to an oil reservoir.

17. The process of claim 2 for the preparation of methanol, wherein such an amount of hydrogen is fed to the methanol reactor that $SN>1.9$ is achieved.

18. The process of claim 3 for the preparation of methanol, wherein such an amount of hydrogen is fed to the methanol reactor that $SN>1.9$ is achieved.

* * * * *